United States Patent
Wesolowska et al.

(12)

(10) Patent No.: US 11,191,758 B2
(45) Date of Patent: Dec. 7, 2021

(54) USE OF SELECTIVE SEROTONIN 5-HT$_{1A}$ RECEPTOR AGONISTS FOR TREATING SIDE-EFFECTS OF VMAT INHIBITORS

(71) Applicants: Neurolixis, Labruguiere (FR); Uniwersytet Jagiellonski Collegium Medicum, Cracow (PL)

(72) Inventors: Anna Wesolowska, Cracow (PL); Magdalena Jastrzebska-Wiesek, Cracow (PL); Adrian Newman-Tancredi, Castres (FR); Mark Andrew Varney, Dana Point, CA (US)

(73) Assignees: Neurolixis, Labruguiere (FR); Uniwersytet Jagiellonski Collegium Medicum, Cracow (PL)

( * ) Notice: Subject to any disclaimer, the term of this patent is extended or adjusted under 35 U.S.C. 154(b) by 29 days.

(21) Appl. No.: 16/630,938

(22) PCT Filed: Jul. 20, 2018

(86) PCT No.: PCT/EP2018/069731
§ 371 (c)(1),
(2) Date: Jan. 14, 2020

(87) PCT Pub. No.: WO2019/016357
PCT Pub. Date: Jan. 24, 2019

(65) Prior Publication Data
US 2020/0155535 A1    May 21, 2020

(30) Foreign Application Priority Data

Jul. 20, 2017 (EP) .................... 17305969

(51) Int. Cl.
| | |
|---|---|
| *A61K 31/4545* | (2006.01) |
| *A61P 25/08* | (2006.01) |
| *A61K 9/00* | (2006.01) |
| *A61K 31/135* | (2006.01) |
| *A61K 31/428* | (2006.01) |
| *A61K 31/4418* | (2006.01) |
| *A61K 31/4433* | (2006.01) |
| *A61K 31/496* | (2006.01) |
| *A61K 31/506* | (2006.01) |

(52) U.S. Cl.
CPC ........ *A61K 31/4545* (2013.01); *A61K 9/0053* (2013.01); *A61K 31/135* (2013.01); *A61K 31/428* (2013.01); *A61K 31/4418* (2013.01); *A61K 31/4433* (2013.01); *A61K 31/496* (2013.01); *A61K 31/506* (2013.01); *A61P 25/08* (2018.01)

(58) Field of Classification Search
CPC .................................................. A61K 31/4545
USPC ....................................................... 514/256
See application file for complete search history.

(56) References Cited

U.S. PATENT DOCUMENTS

2015/0313903 A1    11/2015    During

FOREIGN PATENT DOCUMENTS

| WO | 1998022459 | 5/1998 |
| WO | 2013/152105 | 10/2013 |
| WO | 2016/005527 | 1/2016 |

OTHER PUBLICATIONS

Kasahara, Life Sciences, 1993, 52 (22), 1741-1749.*
Ahlenius, Pharmacology, and Toxico, 1993, 72(6), 398-406.*
S. Ahlenius et al., "Effects of s-fil6 Receptor Agonists on Patterns of Rat Motor Activity in Relation to Effects on Florebrain Monoamine Synthes", Pharmacology & Toxicology, 1993, pp. 398-40, vol. 72, Denmark.
L. A. Bruins Slot et al., "Differential profile of antipsychotics at serotonin 5-HT1A and dopamine D2S receptors coupled to extracellular signal-regulated kinase", European Journal of Pharmacology, Feb. 21, 2006, pp. 63-70, vol. 534, Elsevier B.V.
L. Brusa et al., "Tetrabenazine improves levodopa-induced peak-dose dyskinesias in patients with Parkinson's disease", Functional Neurology, 2013, pp. 101-105, vol. 28(2).
A. Carlsson, "The Occurrence, Distribution and Physiological Role of Catecholamines in the Nervous System", Symposium on Catecholmines, Pharmacological Reviews, 1959, pp. 490-493, vol. 11.
P. Celada et al., "Serotonin 5-HT1A Receptors as Targets for Agents to Treat Psychiatric Disorders: Rationale and Current Status of Research", CNS Drugs, Jun. 12, 2013, Springer International Publishing, Switzerland.
S. Duty et al., "Animal models of Parkinson's disease: a source of novel treatments and clues to the cause of the disease", British Journal of Pharmacology, 2011, pp. 1357-1391, vol. 164, The British Pharmacological Society, www.brjpharmacol.org.
L. D. Fuenmayor et al., "The Influence of Cerebral 5-Hydroxytryptamine on Catalepsy Induced by Brain-Amine Depleting Neuroleptics or by Cholinomimetics", British Journal of Pharmacology, 1979, pp. 309-318, vol. 67, Macmillan Journals Ltd.
L. D. Fuenmayor et al., "Production of Catalepsy and Depletion of Brain Mono-Amines by a Butyrophenone Derivative", British Journal of Pharmacology, 1979, pp. 115-122, vol. 67, Macmillan Journals Ltd.

(Continued)

*Primary Examiner* — Nizal S Chandrakumar
(74) *Attorney, Agent, or Firm* — Zaretsky Group PC; Howard Zaretsky

(57) ABSTRACT

The present invention relates to the reduction of the side-effects induced by tetrabenazine or other inhibitors of vesicular monoamine transporter (VMAT), in the treatment of central nervous system disorders such as Huntington's disease, L-DOPA-induced dyskinesias in Parkinson's disease, Tourette's syndrome or tardive dyskinesia. The invention comprises administering to a patient in need thereof an effective amount of activates selective serotonin 5-HT$_{1A}$ receptors agonist, whereby the side-effects of depression or Parkinsonism induced by tetrabenazine or other VMAT inhibitors are minimized.

6 Claims, 3 Drawing Sheets

(56) References Cited

OTHER PUBLICATIONS

J. P. Henry et al., "Biochemistry and Molecular Biology of the Vesicular Monoamine Transporter from Chromaffin Granules", The Journal of Experimental Biology, 1994, pp. 251-262, vol. 196, The Company of Biologists Limited, Great Britain.

T. Ishibashi et al., "Antiparkinsonian Actions of a selective 5-HT1A agonist, tandospirone, in Rats", Biogenic Amines, 2004, pp. 329-338, vol. 18, No. 3-6, VSP, www.vsppub.corn.

J. Jankovic et al., "Tetrabenazine therapy of dystonia, chorea, tics, and other dyskinesias", Neurology, Mar. 1988, pp. 391-394, vol. 38.

C. Kenney et al., "Is History of Depression a Contraindication to Treatment With Tetrabenazine?", Clinical Neuropharmacology, Sep.-Oct. 2006, pp. 259-264, vol. 29, No. 5, Lippincott Williams & Wilkins.

A. Newman-Tancredi et al., Novel antipsychotics activate recombinant human and native rat serotonin 5-HT1A receptors: affinity, efficacy and potential implications for treatment of schizophrenia, International Journal of Neuropsychopharmacology, 2005, pp. 341-356, vol. 8, CINP.

J. R. Nickell et al., "Synthesis and in vitro evaluation of water-soluble 1,4-diphenethylpiperazine analogs as novel inhibitors of the vesicular monoamine transporter-2", Bioorganic & Medicinal Chemistry Letters, 2016, pp. 4441-4445, vol. 26, Elsevier Ltd., www.elsevier.com.

J. R. Nickell et al., "GZ-793A inhibits the neurochemical effects of methamphetamine via a selective interaction with the vesicular monoamine transporter-2", European Journal of Pharmacology, 2017, pp. 143-149, vol. 795, Elsevier B.V., www.elsevier.com.

Y. Ohno et al., "New insight into the therapeutic role of the serotonergic system in Parkinson's disease", Progress in Neurobiology, 2015, pp. 104-121, vol. 134, Elsevier Ltd., www.elsevier.com.

W. G. Ondo et al., "Exploring the Relationship Between Parkinson Disease and Restless Legs Syndrome", Arch Neurol, Mar. 2002, pp. 421-424, vol. 59, American Medical Association, www.archneurol.com.

W. G. Ondo et al., "Tetrabenazine Treatment for Tardive Dyskinesia: Assessment by Randomized Videotape Protocol", American Journal of Psychiatry, Aug. 1999, pp. 1279-1281, vol. 156.

P. Diana, "Tetrabenazine in the treatment of Huntington's disease", Neuropsychiatric Disease and Treatment, 2007, pp. 545-551, vol. 3(5), Dove Medical Press Limited.

D. J. Pettibone et al., "Tetrabenazine-lnduced Depletion of Brain Monoamines: Characterization and Interaction with Selected Antidepressants", European Journal of Pharmacology, 1984, pp. 425-430, vol. 102, Elsevier Science Publishers B.V.

S. J. Podurgiel et al., "The Vesicular Monoamine Transporter (VMAT-2) Inhibitor Tetrabenazine Induces Tremulous Jaw Movements in Rodents: Implications for Pharmacological Models of Parkinsonian Tremor", Neuroscience, 2013, pp. 507-519, vol. 250, IBRO, Elsevier Ltd.

R. D. Porsolt et al., "Behavioural Despair in Rats: A New Model Sensitive to Antidepressant Treatments", European Journal of Pharmacology, 1978, pp. 379-391, vol. 47, Elsevier/North-Holland Biomedical Press.

E. P. M. Prinssen et al., "The cataleptogenic effects of the neuroleptic nemonapride are attenuated by its 5-HT1A receptor agonist properties", European Journal of Pharmacology, 1998, pp. 189-192, vol. 356, Elsevier Science B.V.

E. Storey, "Tardive Tremor", Movement Disorders, 1997, pp. 808-810, vol. 12, No. 5.

A. H. Vaidya et al., "Oral Buspirone Causes a Shift in the Dose-Response Curve Between the Elevated-Plus Maze and Vogel Conflict Tests in Long-Evans Rats: Relation of Brain Levels of Buspirone and 1-PP to Anxiolytic Action", Methods and Findings in Experimental and Clinical Pharmacology, 2005, pp. 245-255, vol. 27(0), Prous Science.

C. Kenney et al., "Tetrabenazine in the treatment of hyperkinetic movement disorders", Expert Review of Neurotherapeutics, 2006, pp. 7-16, vol. 6(1), Future Drugs Ltd., www.future-drugs.com.

Ishibashi T et al, "Antiparkinsonian actions of a selective 5-HT1A agonist, tandospirone, in rats", Biogenic Amines 2004 NL,vol. 18, No. 3-6, 2004, p. 329-338, XP009501787.

Ahlenius S et al, "Effects of 5-HT1A Receptor Agonists on Patterns of Rat Motor Activity in Relation to Effects on Forebrain Monoamine Synthesis", Pharmacology and Toxico, Munksgaard International Publishers, Copenhagen, DK,vol. 72, No. 6, Jan. 1, 1993 (Jan. 1, 1993), p. 398-406, XP008030781.

Mignon L et al, "Postsynaptic 5-HT1A receptors mediate an increase in locomotor activity in the monoamine-depleted rat", Psychopharmacology 2002 DE,vol. 163, No. 1, 2002, p. 85-94, XP009501775.

Karl Strecker et al, "The 5-HT1A-receptor agonist flibanserin reduces drug-induced dyskinesia in RGS9-deficient mice", Journal of Neural Transmission ; Basic Neurosciences, Genetics and Immunology, Parkinson's Disease and Allied Conditions, Alzheimer's Disease and Adolescent Psychiatry Related Disorders, Biological Psychiatry, Biological Child and Adolescent Psychiat,vol. 119, No. 11, May 10, 2012 (May 10, 2012), p. 1351-1359, XP035128114.

Lockwood J T et al, "Emerging drugs for antipsychotic-induced tardive dyskinesia: Investigational drugs in Phase II and Phase III clinical trials", Expert Opinion on Emerging Drugs Jul. 3, 2015 Taylor and Francis Ltd GBR,vol. 20, No. 3, Jul. 3, 2015 (Jul. 3, 2015), p. 407-421, XP002775890.

Luciano Angelo Y et al, "Treatment of myoclonus-dystonia syndrome with tetrabenazine", Parkinsonism and Related Disorders,vol. 20, No. 12, 2014, p. 1423-1426, XP029098696.

Kasahara K I et al, "Role of 5-HT"1"A receptors in the forced swimming wheel test in reserpine-treated mice", Jan. 1, 1993 (Jan. 1, 1993), vol. 52, No. 22, p. 1741-1749, XP025549930.

Anonymous, "Xenazine (R) (Tetrabenazine) Tablets", May 2008 (May 2008), Prestwick Phamaceuricals Retrieved from the Internet: URL:https://www.accessdata.fda.gov/drugsatfda_docs/label/2008/021894lbl.pdf, XP002784606.

Anonymous, "Austedo TM (Deutetrabenazine) tablets for oral use", Apr. 2017 (Apr. 2017), Teva Pharmaceuticals Retrieved from the Internet: URL:https://www.accessdata.fda.gov/drugsatfda_docs/label/2017/208082s000lbl.pdf, XP002784607.

International Search Report and Written Opinion issued with respect to PCT/EP2018/069731 dated Oct. 1, 2018.

Blier, et al., Selective Activation of Postsynaptic 5-HT1A Receptors Induces Rapid Antidepressant Response, Neuropsychopharmacology, 1997, pp. 333-338, vol. 16, No. 5, Elsevier Science Inc., New York, NY.

* cited by examiner

USE OF SELECTIVE SEROTONIN 5-HT$_{1A}$ RECEPTOR AGONISTS FOR TREATING SIDE-EFFECTS OF VMAT INHIBITORS

FIELD OF THE INVENTION

The present invention relates to the reduction of the side-effects induced by inhibitors of the function of vesicular monoamine transporter (VMAT) such as tetrabenazine, a class of drugs used in the treatment of central nervous system disorders such as Huntington's disease, L-DOPA-induced dyskinesias in Parkinson's disease, Tourette's syndrome or tardive dyskinesia. The invention comprises administering to a patient in need thereof an effective amount of a selective serotonin 5-HT$_{1A}$ receptor agonist such as befiradol, whereby the side-effects of depression or Parkinsonism induced by said VMAT inhibitors are minimized.

BACKGROUND OF THE INVENTION

Movement Disorders

Movement disorders are conditions of the nervous system that affect the intentional ability to produce and control body movement, its speed, fluency, quality, and ease. They usually manifest as abnormal, involuntary movements (dyskinesia) or postures (akinesia) such as chorea (involuntary, rapid, irregular, jerky movements), ballismus (involuntary movements similar to chorea but more violent, explosive), dystonia (involuntary sustained muscle spasms, usually producing twisting, repetitive movements or abnormal postures and positions), myoclonus (twitching or intermittent muscular spasms producing rapid, brief, movements), athetosis (repetitive involuntary, slow, sinuous, writhing movements, especially severe in the hands), akathisia (inability to sit still or remain motionless), ataxia (lack of coordination, often producing jerky movements), syncinesia (the occurrence simultaneously of both voluntary and involuntary movements), tics (involuntary muscle contractions that interrupt normal activities), bradykinesia (slowness or poverty of movement) or tremor (involuntary rhythmic muscle contraction and relaxation involving to and from movements).

Such symptoms can occur as a consequence of inherited or acquired diseases, and/or they can result from medical treatments. They are often associated with basal ganglia dysfunction and impaired regulation of dopamine neurotransmission. Some examples of movement disorders that encompass some of the above symptoms and include the following.

An example of a movement disorder is Huntington's disease (HD), a rare, inherited disease that causes chronic progressive chorea and problems with movement coordination. The initial consequences include degeneration of medium spiny neurons in the striatum, which is important in the control of movement. In the early stage of HD, slowing of movements, chorea, and occasional loss of balance are significant symptoms. The motor disorder of HD is severely disabling and manifests as involuntary bodily movements as well as abnormal control of ocular movements. Chorea is the most common involuntary movement in patients with HD. As the disease progresses, chorea tends to diminish, as Parkinsonism (i.e. bradykinesia, tremor) and dystonia emerge. Balance and walking problems become more serious and incapacitating.

Another example of a movement disorder is Parkinson's disease, which is characterized by pronounced movement impairment, including bradykinesia, rigidity and/or tremor. The symptomatic therapy of Parkinson's disease mainly consists in administering to the patient dopamine-replacing agents that alleviates motor symptoms and improve their quality of life. Levodopa (3,4-hydroxyphenylalanine) which remains the gold standard for treatment of Parkinson's disease, acts as a dopamine prodrug, which is metabolized into dopamine in the brain. Dopamine, in turn, activates dopamine receptors. Direct-acting dopamine receptor agonists such as bromocriptine, lisuride, pramipexole, ropinirole and pergolide are also used mainly in the earlier stages of Parkinson's disease. However, following long-term use, dopamine agonist or Levodopa dopamine-replacement therapies become less efficacious, with the patients switching alternatively from responding periods (termed "ON") to non responding periods (termed "OFF"), and the appearance of side-effects such as other involuntary movements, called dyskinesias. These dyskinesias are troublesome and can seriously impact the quality of life of the patients.

Other examples can be cited such as Tourette's syndrome (an inherited disorder characterized by multiple motor and vocal tics), dystonia (a disorder associated with slowness of movement, poor balance and difficulty moving around) and tardive dyskinesia (a disorder that can result from the use of a number of different pharmacological agents, such as antipsychotic drugs that target the dopamine system, and associated with facial tics and movements of the jaw, lips and tongue).

Another example includes tardive dyskinesia. Tardive dyskinesias (TDs) are involuntary movements of the tongue, lips, face, trunk, and extremities that occur in patients treated with long-term dopaminergic antagonist medications. TD can be associated with the use of neuroleptics, and people with schizophrenia and other neuropsychiatric disorders are especially vulnerable to the development of TDs after exposure to conventional neuroleptics, anticholinergics, toxins, substances of abuse, and other agents.

TDs are most common in patients with schizophrenia, schizoaffective disorder, or bipolar disorder who have been treated with antipsychotic medication for long periods, but they occasionally occur in other patients as well. For example, people with fetal alcohol syndrome, other developmental disabilities, and other brain disorders are vulnerable to the development of TDs, even after receiving only a single dose of the causative agent.

VMAT Inhibitor, Tetrabenazine in Clinical Use

Although many treatments for movement disorders have been investigated over the past years, some of the approved therapies exhibit either poor efficacy and/or tolerability issues. In particular, the benzoquinolizine derivative tetrabenazine (TBZ; (SS,RR)-3-Isobutyl-9,10-dimethoxy-1,3,4,6,7,11b-hexahydro-pyrido[2,1-a]isoquinolin-2-one) is an FDA-approved pharmacological agent for treatment of chorea associated with HD, although it has also been used in a multitude of movement disorders characterized by abnormal and/or hyperkinetic involuntary movements, drug induced or primary: L-DOPA-induced dyskinesia (Brusa, L. et al., 2013 Funct Neurol. 28, 101-5) tardive dyskinesia (Ondo, W. G., 1999 Am J Psychiatry. 156, 1279-81), dystonia (Jankovic, J., 1988 Neurology. 38, 391-4, Paleacu, D., 2007 Neuropsychiatr Dis Treat. 3, 545-51), tremor (Storey, E., 1997 Mov Disord. 12, 808-10), choreic syndromes (Ondo, W. G., 2002 Arch Neurol. 59, 421-4) and tic disorders (Jankovic, J., 1988 Neurology. 38, 391-4).

The mechanism of action of TBZ has been well characterized (Pettibone, D. J., 1984 Eur J Pharmacol. 102, 431-6). TBZ acts mainly as a reversible high-affinity inhibitor of monoamine uptake into granular vesicles of neurons by binding to the vesicular monoamine transporter (VMAT), leading to depletion of the monoamine neurotransmitters, dopamine, serotonin and norepinephrine. VMATs are found in a variety of cell types throughout the body, with two principal subtypes: VMAT1 is found exclusively in neuroendocrine cells, in contrast to VMAT2, which is also found in the peripheral and central nervous systems. TBZ preferentially inhibits VMAT2.

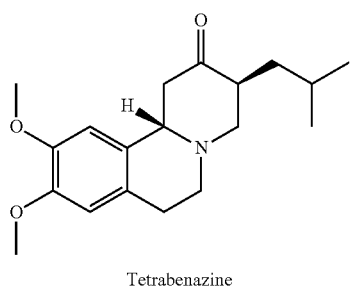 [SMILES: COc1cc2c(cc1OC)[C@@H]1CC(=O)[C@@H](CC(C)C)CN1CC2]

Tetrabenazine

VMAT2 is also inhibited by deutetrabenazine, dihydrotetrabenazine, GZ-793A (3-[(2R,6S)-2,6-Bis[2-(4-methoxyphenypethyl)ethyl]-1-piperidinyl]-(2R)-1,2-propanediol) (Nickell, J. R., et al., 2016 Bioorg Med Chem Lett. 26, 4441-5), 1,4-diphenethylpiperazines derivatives (Nickell, J. R., et al., 2016 Bioorg Med Chem Lett. 26, 4441-5), valbenazine ((2R,3R,11bR)-3-Isobutyl-9,10-dimethoxy-1,3,4,6,7,11b-hexahydro-2H-pyrido[2,1-a]isoquinolin-2-yl L-valinate) and reserpine (methyl (3β,16β, 17α, 18β,20α)-11,17-dimethoxy-18-[(3,4,5-trimethoxybenzoyl)oxy]yohimban-16-carboxylate).

Side-Effects of the VMAT Inhibitor Tetrabenazine

TBZ and other VMAT inhibitors exhibit some potentially serious side-effects due to induction of depression and suicidality. These side-effects markedly limit the clinical utility of TBZ in Huntington's disease (Kenney, C., 2006 Expert Rev Neurother. 6, 7-17; Kenney, C., et al., 2006 Clin Neuropharmacol. 29, 259-64): physicians must discuss this risk with individuals and their caregivers, and clinical monitoring must be provided. The drug labels contain blackboxed warning which highlights the risk of depression and suicidality induction by TBZ and deutetrabenazine.

Warning label for TBZ (Xenazine™; Oceanside, 2016):

Warning: Depression and Suicidality

Increases the risk of depression and suicidal thoughts and behavior (suicidality) in patients with Huntington's disease.

Balance risks of depression and suicidality with the clinical need for control of chorea when considering the use of tetrabenazine tablets.

Monitor patients for the emergence or worsening of depression, suicidality, or unusual changes in behavior.

Inform patients, caregivers and families of the risk of depression and suicidality and instruct to report behaviors of concern promptly to the treating physician.

Exercise caution when treating patients with a history of depression or prior suicide attempts or ideation.

Tetrabenazine tablets are contraindicated in patients who are actively suicidal, and in patients with untreated or inadequately treated depression."

Warning label for deutetrabenazine (Austedo™; Teva, 2017)

"WARNING: DEPRESSION AND SUICIDALITY

AUSTEDO can increase the risk of depression and suicidal thoughts and behavior (suicidality) in patients with Huntington's disease. Anyone considering the use of AUSTEDO must balance the risks of depression and suicidality with the clinical need for treatment of chorea. Closely monitor patients for the emergence or worsening of depression, suicidality, or unusual changes in behavior. Patients, their caregivers, and families should be informed of the risk of depression and suicidality and should be instructed to report behaviors of concern promptly to the treating physician.

Particular caution should be exercised in treating patients with a history of depression or prior suicide attempts or ideation, which are increased in frequency in Huntington's disease. AUSTEDO is contraindicated in patients who are suicidal, and in patients with untreated or inadequately treated depression."

The induction of depression-like behavior by TBZ can be modeled in rodent experiments such as the classic model of depression, the forced swim test (Porsolt, R. D., et al., 1978 Eur J Pharmacol 47, 379-91).

A second type of side-effects induced by TBZ and other VMAT inhibitors is Parkinsonism, which is a clinical syndrome characterized by tremor, bradykinesia, rigidity, and postural instability. The drug label contains the following warning which highlights the risk of Parkinsonism induction by TBZ (Xenazine™; Oceanside, 2016):

"Tetrabenazine tablets can cause Parkinsonism. In a 12-week double-blind, placebo-controlled study in patients with chorea associated with HD, symptoms suggestive of Parkinsonism (i.e., bradykinesia, hypertonia and rigidity) were observed in 15% of tetrabenazine-treated patients compared to 0% of placebo-treated patients. In 48-week and 80-week open-label studies, symptoms suggestive of Parkinsonism were observed in 10% and 3% of tetrabenazine-treated patients, respectively. Because rigidity can develop as part of the underlying disease process in Huntington's disease, it may be difficult to distinguish between this drug-induced side-effect and progression of the underlying disease process. Drug-induced Parkinsonism has the potential to cause more functional disability than untreated chorea for some patients with Huntington's disease. If a patient develops Parkinsonism during treatment with tetrabenazine tablets, dose reduction should be considered; in some patients, discontinuation of therapy may be necessary."

Similarly, the following warning from deutetrabenazine (Austedo™) also highlights a risk of Parkinsonism (Teva, 2017):

"AUSTEDO may cause Parkinsonism in patients with Huntington's disease. Because rigidity can develop as part of the underlying disease process in Huntington's disease, it may be difficult to distinguish between this potential drug-induced adverse reaction and progression of the underlying disease process. Drug-induced Parkinsonism has the potential to cause more functional disability than untreated chorea for some patients with Huntington's disease. If a patient develops Parkinsonism during treatment with AUSTEDO, the AUSTEDO dose should be reduced; some patients may require discontinuation of therapy."

The induction of Parkinsonism by TBZ can be modeled in rodent experiments which measure catalepsy (Fuenmayor, L. D., 1979a. Br J Pharmacol. 67, 309-18; Fuenmayor, L. D., 1979b. Br J Pharmacol. 67, 115-22; Podurgiel, S. J., et al., 2013 Neuroscience. 250, 507-19). Other VMAT inhibitors, such as reserpine (Henry et al., 1994), also produce Parkinsonism, both in animal models (Duty, S., 2011 Br J Pharmacol. 164, 1357-91) and in human (Carlsson, A., 1959 Pharmacol Rev. 11, 490-3)

Overall, these studies show that TBZ can cause or aggravate serious side-effects including depression, suicidality and Parkinsonism. Thus, there is a great need of finding agents that would minimize side-effects of TBZ when treating patients with movement disorders.

SUMMARY OF THE INVENTION

Serotonin 5-$HT_{1A}$ Receptor Agonists as Therapeutics for Side-Effects Induced by VMAT Inhibitors 5-$HT_{1A}$ agonists may be useful for treating several mood disorders such as depression and anxiety (Celada, P., 2013 CNS drugs. 27, 703-16). The existence of a link between serotonergic mechanisms, including subtypes of serotonin receptors such as the 5-$HT_{1A}$ sub-type, and movement disorders has been discussed in scientific reports over recent years. Consequently, the potential field of application of compounds that activate 5-$HT_{1A}$ receptors has been extended to treating movement disorders (Ohno, Y., et al., 2015 Prog Neurobiol. 134, 104-21).

In the international application WO2016/005527, the company Pierre Fabre describes the use of formulations of befiradol to ameliorate and/or prevent some aspects of movement disorders, such as extrapyramidal side-effects associated with neuroleptics treatment, dyskinesia that arise from long-term Levodopa therapy in Parkinson's disease or involuntary movement in Huntington's disease. However, no mention is made of VMAT inhibitor-induced side-effects.

On the other hand, attempts have been made to alleviate the side-effects that develop upon TBZ or other VMAT inhibitors. For instance, the international application WO2013-152105 A1 describes novel pharmaceutical compositions comprising a therapeutically effective combination of a dopaminergic stabilizer known as pridopidine, and the inhibitor of the vesicular monoamine transporter type 2 (VMAT), TBZ. The pharmaceutical compositions are considered to be useful for improving the symptomatic therapeutic effects, and for reducing the clinically-limiting effects of TBZ in the treatment of movement disorders, notably those associated with Huntington's disease, Gilles de la Tourette's syndrome, or tardive dyskinesia.

In the application of US Pat. US 2015/0313903, the company Ovid Pharmaceuticals discloses a (1-piperidinylalkyl) pyrimidinone derivative, preferably ritanserin or a pharmaceutically acceptable salt thereof, to be administered to a subject in combination with a conventional treatment for Huntington's disease, such as a dopamine blocker, amantadine or TBZ to help reduce abnormal behaviors and movements. However, ritanserin is a serotonin 5-$HT_{2A}$ receptor antagonist and does not interact with 5-$HT_{1A}$ receptors.

Ishibashi et al (Biogenic amines, 2004, 18, 3-6, 329-338) and Ahlenius et al (Pharmacologyandtoxico, 72, 6, 1993, 398-406) report the action of 5-$HT_{1A}$ receptor agonists on locomotor activity in reserpine treated rats.

Several molecular and pharmaceutical differences are known between reserpine and tetrabenazine: reserpine is a non-selective VMAT inhibitor whereas tetrabenazine is a VMAT2 inhibitor. Further, contrary to reserpine, tetrabenazine-binding is reversible and the half-life of reserpine is very long compared to that of tetrabenazine. Therefore, the side-effects induced by reserpine and their alleviation cannot be extrapolated to tetrabenazine.

It is notable that no patent applications have been identified that describe the use of 5-$HT_{1A}$ receptor agonists in the treatment of side-effects induced by TBZ or other VMAT inhibitors. The prior art concerning the use of 5-$HT_{1A}$ receptor agonists for the treatment of VMAT inhibitor-induced side-effects is, therefore, currently nonexistent.

The inventors have discovered that agonists at the 5-$HT_{1A}$ receptor subtype are highly effective for preventing or reducing depressive symptoms and parkinsonian symptoms induced by TBZ, thereby potentially improving the therapeutic utility of VMAT inhibitors in system disorders such as Huntington's disease, L-DOPA-induced dyskinesias in Parkinson's disease, Tourette's syndrome or tardive dyskinesia.

Accordingly, a first embodiment of the invention is to provide a use of a compound which enhances 5-$HT_{1A}$ receptor activation for the manufacture of a medicament that prevents or reduces the motor side-effects such as Parkinsonism that arise as a consequence of, or are aggravated by, therapy using VMAT inhibitors.

A second embodiment of the invention is to provide a use of a compound which enhances 5-$HT_{1A}$ receptor activation for the manufacture of a medicament that prevents or reduces the depressive symptoms that arise as a consequence of, or are aggravated by, therapy using VMAT inhibitors.

A third embodiment of the invention is to provide a use of a compound which enhances 5-$HT_{1A}$ receptor activation for the manufacture of a medicament that prevents or reduces the suicidal thoughts and successful suicide that arise as a consequence of, or are aggravated by, therapy using VMAT inhibitors.

A fourth embodiment of the invention is to provide a composition for use in the prevention or reduction of the motor side-effects such as Parkinsonism that arise as a consequence of, or are aggravated by, therapy using VMAT inhibitors comprising a therapeutically effective amount of a compound which enhances 5-$HT_{1A}$ receptor activation, and a pharmaceutically acceptable vehicle.

A fifth embodiment of the invention is to provide a composition for use in the prevention or reduction of depressive symptoms that arise as a consequence of, or are aggravated by, therapy using VMAT inhibitors comprising a therapeutically effective amount of a compound which enhances 5-$HT_{1A}$ receptor activation, and a pharmaceutically acceptable vehicle.

A sixth embodiment of the invention is to provide a composition for use in the prevention or reduction of suicidal thoughts and successful suicide that arise as a consequence of, or are aggravated by, therapy using VMAT inhibitors comprising a therapeutically effective amount of a compound which enhances 5-$HT_{1A}$ receptor activation, and a pharmaceutically acceptable vehicle.

A seventh embodiment of the invention is to provide a method for the prevention or reduction of motor fluctuations (such as Parkinsonism) that arise as a consequence of, or are aggravated by, therapy using VMAT inhibitors comprising administering to a person in need of such treatment a therapeutically effective amount of a compound which enhances 5-$HT_{1A}$ receptor activation.

An eighth embodiment of the invention is to provide a method for the prevention or reduction of depressive symptoms that arise as a consequence of, or are aggravated by, therapy using VMAT inhibitors comprising administering to a person in need of such treatment a therapeutically effective amount of a compound which enhances 5-$HT_{1A}$ receptor activation.

A ninth embodiment of the invention is to provide a method for the prevention or reduction of suicidal thoughts and successful suicide that arise as a consequence of, or are aggravated by, therapy using VMAT inhibitors comprising administering to a person in need of such treatment a therapeutically effective amount of a compound which enhances 5-HT$_{1A}$ receptor activation.

Thus, according to the present invention, known 5-HT$_{1A}$ receptor agonists may be used as an adjunct or alternatively may be given in combination with one or more VMAT inhibitors for the treatment of side-effects induced by TBZ or other VMAT inhibitors, enabling the patient to better tolerate and therefore benefit from VMAT inhibitor therapy. Examples of 5-HT$_{1A}$ receptor agonists that can be used in the pharmaceutical compositions of this invention include, but are not limited to: (±)8-OH-DPAT, tandospirone, repinotan, flesinoxan, flibanserin, sarizotan, xaliproden, as well as befiradol, [(3-Chloro-4-fluoro-phenyl)-[4-fluoro-4-{[(5-methyl-pyridin-2-ylmethyl)-amino]-methyl}piperidin-1-yl]methanone] (described in WO98/22459), derivative 1a (3-chloro-4-fluorophenyl-[4-fluoro-4-[[(5-methylpyrimidin-2-ylmethyl)amino]methyl]piperidin-1-yl]methanone; described in WO2003/106449 A1) and derivative 1b [(3-Chloro-4-fluoro-phenyl)-[4-fluoro-4-{[(5-methyl-2-methyl-amino-pyridin-2-ylmethyl)-amino]-methyl}piperidin-yl] methanone] described in WO98/22459. Befiradol, 1a and 1b are represented by the general formula (I):

(I)

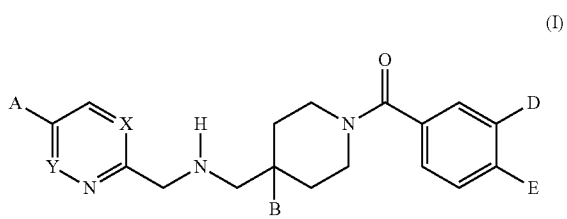

Wherein X represents a carbon atom linked to a hydrogen atom (CH) or a nitrogen atom; Y represents a carbon atom linked to a hydrogen atom (CH) or a nitrogen atom; A represents a methyl, fluoromethyl, cyano, hydroxyl or methoxy radical or a chlorine or fluorine atom, with the proviso, that when A is a methyl radical (CH3) and X and Y simultaneously represent a carbon atom linked to a hydrogen atom, then B necessarily represents a chlorine atom; B represents a chlorine atom or a fluorine atom; D represents a hydrogen atom, a chlorine atom, a fluorine atom, a cyano group or a trifluoromethyl group, E represents a hydrogen, fluorine or chlorine atom.

Among the compounds of formula (I), the preferred ones for use according to the invention are: befiradol, [(3-Chloro-4-fluoro-phenyl)-[4-fluoro-4-{[(5-methyl-pyridin-2-ylmethyl)-amino]-methyl}piperidin-1-yl]methanone], derivative 1a (3-chloro-4-fluorophenyl-[4-fluoro-4-[[(5-methylpyrimidin-2-ylmethyl)amino]methyl]piperidin-1-yl]methanone) and derivative 1b [(3-Chloro-4-fluoro-phenyl)-[4-fluoro-4-{[(5-methyl-2-methylamino-pyridin-2-ylmethyl)-amino]-methyl}piperidin-1-yl]methanone] whose structural formulas are shown below:

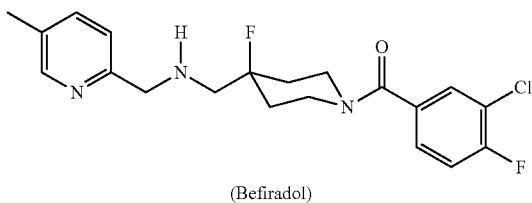

(Befiradol)

(1a)

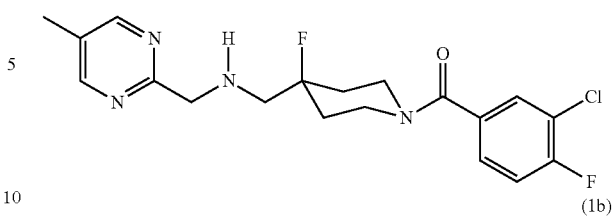

(1b)

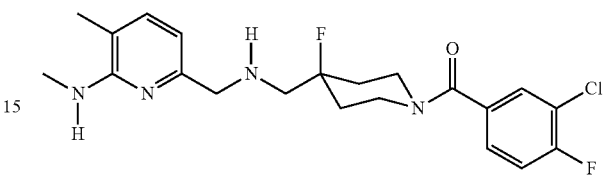

The inventors have also discovered that not all 5-HT$_{1A}$ agonists are equally effective at reducing the side-effects caused by VMAT inhibitors. Without being bound by a theory, it is hypothesized that compounds that exhibit markedly higher agonist efficacy for activation of in vitro signaling at 5-HT$_{1A}$ receptors, such as, for example, befiradol, may be more effective at attenuating the depressive-like symptoms induced by TBZ than those exhibiting a lower level of efficacy, such as buspirone (FIGS. 1 and 3). Likewise, higher efficacy agonists are thought to be more effective at counteracting the catalepsy induced by TBZ than those exhibiting a lower level of efficacy (FIGS. 1 and 4). Thus, among the known 5-HT$_{1A}$ receptor agonists, mentioned above, are preferred for use according to the invention. Typically, these compounds include, but are not limited to: (±)8-OH-DPAT, sarizotan, xaliproden, repinotan, tandospirone, flibanserin and compounds of formula (I).

According to a preferred embodiment, the compound selectively activates the 5-HT$_{1A}$ receptor subtype. By "selectively", it is meant that the compound interacts with the 5-HT$_{1A}$ receptor with a binding affinity which is greater than that observed at other types of 5-HT, dopaminergic, adrenergic receptors or a range of other binding sites. Interactions with receptors other than 5-HT$_{1A}$ can cause side-effects such as, for instance, a worsening of the parkinsonian symptoms caused by the dopamine receptor antagonism, serotonin syndrome caused by activation of 5-HT$_{2A}$ receptors or cardiovascular effects caused by interaction with alpha or beta-adrenergic receptors.

Selective 5-HT$_{1A}$ receptor agonists particularly suitable for treating the pro-depressive and pro-cataleptic effects of TBZ observed in rat experiments which are analogous to the pro-depressive and pro-parkinsonian side-effects of TBZ observed in clinical use, are selected from compounds of formula (I).

The field of application of the present invention therefore relates to treatment and/or prevention of depression and Parkinsonism induced in patients treated with TBZ (Xenazine™) or other VMAT inhibitors such as deutetrabenazine (Austedo™) dihydrotetrabenazine, 1,4-diphenalkylpiperidine derivatives such as GZ-793A (Nickell, J. R., et al., 2017 Eur J Pharmacol. 795, 143-149) and valbenazine (Ingrezza™, NBI-98854) (O'Brien, C. F., et al., 2015 Mov Disord. 30, 1681-7) and reserpine (methyl (3β,16β,17α,18β,20α)-11,17-dimethoxy-18-[(3,4,5-trimethoxybenzoyl)oxy]yohimban-16-carboxylate).

In animal experiments, befiradol, 1a, 1b and (±)8-OH-DPAT reversed depression-like behavior and catalepsy behavior in TBZ-treated rats whereas, surprisingly, buspirone did not. The invention therefore comprises administering to a patient in need thereof an effective amount of befiradol or related compounds that efficaciously and/or selectively activate serotonin 5-HT$_{1A}$ receptors, whereby the side-effects of depression or Parkinsonism induced by TBZ or other VMAT inhibitors are minimized.

Definitions

A "neurotransmitter" as referred to herein, is a substance which transmits signals from a neuron to a target cell across a neuronal synapse.

The terms "serotonin," "5-hydroxytryptamine" and "5-HT" refers to a phenolic amine neurotransmitter produced from tryptophan by hydroxylation and decarboxylation in serotonergic neurons of the central nervous system and enterochromaffin cells of the gastrointestinal tract. Serotonin can bind to and activate serotonin receptors.

The terms "dopamine," "DA" and "4-(2-aminoethyl)benzene-1,2-diol," refer to a catecholamine neurotransmitter and hormone. Dopamine is a precursor of adrenaline (epinephrine) and noradrenaline (norepinephrine). Dopamine can bind to and activate serotonin receptors.

The term "Vesicular monoamine transporter" (VMAT) is used herein to refer to a protein integrated into the membrane of synaptic vesicles of presynaptic neurons. It acts to transport monoamine neurotransmitters—such as dopamine, serotonin, norepinephrine, epinephrine, and histamine—into the vesicles, which release the neurotransmitters into synapses as chemical messages to postsynaptic neurons.

The term "VMAT inhibitor" in the present context refers to a substance capable of binding to VMAT causing it to decrease its capacity to transport monoamine neurotransmitters—such as dopamine, serotonin, norepinephrine, epinephrine, and histamine—into neuronal vesicles.

The terms "VMAT1" and "VMAT2" in the present context refer to subtypes of VMAT proteins, VMAT1 being expressed in neuroendocrine cells and VMAT2 also being located in the peripheral and central nervous systems.

The term "dopamine enhancer", as used herein, refers to a substance capable of enhancing the release or action of dopamine but which as no specific agonist activity at the dopamine receptors themselves. As an example, mention can be made of dopamine precursors, dopamine prodrugs (e.g. L-DOPA), drugs that prevent dopamine levels from decreasing, such as inhibitors of monoamine oxidase (e.g. rasagiline or selegiline), or inhibitors of catechol-O-methyltransferase (e.g. entacapone or tolcapone).

"L-DOPA" or "3,4-dihydroxyphenylalanine" is a precursor to the neurotransmitters dopamine, norepinephrine (noradrenaline), and epinephrine (adrenaline). L-DOPA is able to cross the blood-brain barrier, and is converted to dopamine by the enzyme aromatic L-amino acid decarboxylase (AADC), also known as DOPA decarboxylase (DDC). L-DOPA is used for treatment of Parkinson's disease.

The term "agonist efficacy" is used herein to mean the degree of activation of serotonin 5-HT$_{1A}$ receptors elicited by a test compound in an in vitro assay. Agonist efficacy is expressed herein as a percentage of the effect achieved by the endogenous neurotransmitter, serotonin (5-HT).

The term "agonist" in the present context refers to a substance capable of binding to and activating a receptor. A "5-HT$_{1A}$ receptor agonist" is thus capable of binding to and activating the 5-HT$_{1A}$ receptor. A "dopamine agonist" refers to a substance capable of binding to and activating one or several dopamine receptors.

The term "high efficacy agonist", in the context of the present invention, refers to compounds that activate serotonin 5-HT$_{1A}$ receptors in an in vitro assay to a greater extent than the activation elicited by the partial agonist, buspirone. Examples of commonly-used in vitro assays suitable for determining agonist efficacy include G-protein activation assays, adenylyl cyclase inhibition or Extracellular Regulated Kinase phosphorylation (Bruins Slot et al., 2006 Eur J Pharmacol. 534, 63-70; Newman-Tancredi, A., et al., 2005 Int J Neuropsychopharmacol. 8, 341-56). Examples of high efficacy agonists include, but are not limited to, befiradol, tandospirone, repinotan, flesinoxan, flibanserin, sarizotan and xaliproden.

"Partial agonists" in the present context are compounds able to bind and activate a given receptor, but having only partial agonist efficacy at the receptor relative to that of the endogenous neurotransmitter, 5-HT. Such partial agonists include buspirone, ipsapirone and gepirone.

The term "antagonist" in the present context refers to a substance capable of inhibiting the effect of a receptor agonist.

"Selective 5-HT$_{1A}$ receptor agonists", as used herein, are compounds which exhibit greater binding affinity at 5-HT$_{1A}$ receptors than at other types of 5-HT, dopaminergic, adrenergic receptors or a range of other binding sites. Binding affinity is often expressed as pKi (negative logarithm of the inhibition constant, Ki). In the context of the present invention, a selective agonist has a pKi value for 5-HT$_{1A}$ receptors that is at least 1 log unit greater than the pKi at other receptors, preferentially 2 log units greater than the pKi at other receptors, and more preferentially log 3 units greater than the pKi at other receptors.

The term "patient", as referred to herein, is an individual that may benefit from the administration of compounds or a pharmaceutical composition according to the present invention. Such an individual may suffer from a movement disorder or be in risk of suffering from a movement disorder.

The individual may be any human being, male or female, infant or old. The movement disorder to be treated or prevented in the individual may relate to the age of the individual, the general health of the individual, the medications used for treating the individual and whether or not the individual has a prior history of suffering from diseases or disorders that may have or have induced movement disorders in the individual.

The patient to be treated is typically a mammal, in particular a human being. Treatment of animals, such as mice, rats, dogs, cats, cows, sheep and pigs, is, however, also within the scope of the present invention. The patients to be treated according to the present invention can be of various ages.

The term "active pharmaceutical ingredient", as used herein, refers to the substance used in a finished pharmaceutical product that is biologically active and intended to furnish pharmacological activity in the diagnosis, cure, mitigation, treatment or prevention of disease.

The term "pharmaceutically acceptable derivative" in present context includes pharmaceutically acceptable salts or hydrates or solvates of the said pharmaceutically acceptable salts, which indicate a salt or hydrates or solvates of it which is not harmful to the patient. Such salts include, but are not limited to, pharmaceutically acceptable acid addition salts as well as pharmaceutically acceptable metal salts. A pharmaceutically acceptable derivative further includes prodrugs, or other precursors of a compound which may be biologically metabolized into the active compound, or crystal forms of a compound of the present invention.

The term "therapeutically effective amount" of a compound, as used herein, refers to an amount sufficient to cure, alleviate, prevent, reduce the risk of, or partially arrest the clinical manifestations of a given disease or disorder and its complications. An amount adequate to accomplish this is defined as a "therapeutically effective amount".

The expression "equivalent to [ . . . ] of compound base" refers to the corresponding amount of compound, if it was administered in its base, non-salified form. For example, 0.65 mg of befiradol fumarate is equivalent to 0.5 mg to befiradol base.

As used herein, the term "pharmaceutical composition" refers to a composition comprising active pharmaceutical ingredient or a pharmaceutically acceptable derivative thereof and at least one pharmaceutically acceptable excipient.

The expression "pharmaceutically acceptable excipient" in the context of the present invention comprises any substance other than the active compound in a pharmaceutical composition, such as any diluent, additive, adjuvant or excipient. As an example, mention may be made of preservatives, fillers, disintegrators, wetting agents, emulsifiers, dispersants, antibacterial or antifungal agents, solid carriers, flavoring agents, solubilizers, lubricants, glidants, binders, antiadherents, sorbents, encapsulating/coating materials or other agents that would allow a controlled release of the active compound.

The terms "sustained release", "controlled release" or "modified release" in the present context refers to compositions that release active pharmaceutical ingredient (and optionally additional active ingredients) at a time other than promptly after administration, e.g., over an extended period of time that exceeds the duration of active pharmaceutical ingredient release from conventional immediate release compositions.

The terms "treatment" and "treating" as used herein refer to the management and care of a patient for the purpose of combating a condition, disease or disorder. The term is intended to include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications.

The term "movement disorder", as used herein, refers to any condition that affects the movements of a patient, from any origin. For example, movement disorder can refer to a condition of the nervous system that affects the intentional ability to produce and/or control body movements or postures. As examples, mention may be made of Huntington's disease, Parkinson's disease, L-DOPA-induced dyskinesia, Tourette's syndrome, tardive dyskinesia, dystonia, essential tremor, choreic syndromes and tic disorders.

BRIEF DESCRIPTION OF THE DRAWINGS

FIG. 1 illustrates the stimulation by 5-$HT_{1A}$ receptor agonists of [$^{35}$S]GTPγS binding to rat hippocampal membranes in vitro In an in vitro assay, 5-HT efficaciously stimulated G-protein activation determined by [$^{35}$S]GTPγS binding to rat hippocampal membranes. High concentrations (10 μM) of befiradol, 1a and 1b exhibited high agonist efficacy. That is, they stimulated [$^{35}$S]GTPγS binding with Emax values that were greater than 90% relative to 5-HT. In contrast, buspirone exhibited lower efficacy and (±)8-OH-DPAT exhibited intermediate efficacy. Data are means±s.e.m. of at least 3 determinations. Abbreviations: Bef=befiradol, 8OH=(±)8-OH-DPAT, Bus=buspirone.

FIG. 2 illustrates the effect of TBZ on duration of rat immobility behavior in the Forced Swim test Immobility time in the rat Forced Swim Test, is an in vivo behavioral measure of depressive-like behavior (Porsolt, R. D., et al., 1978 European journal of pharmacology. 47, 379-91). The Figure shows means±s.e.m. values of immobility for vehicle-treated rats (left-hand bar) and for rats that were treated with TBZ (1.5 mg/kg i.p.; right-hand bar). The latter showed significantly increased immobility, indicating that TBZ has a pro-depressive effect in this rodent model.

FIG. 3 illustrates the effects of 5-$HT_{1A}$ receptor agonists on immobility behavior on rats treated with TBZ in the Forced Swim test The rat Forced Swim Test (FST), is an in vivo behavioral model of depressive behavior (Porsolt, R. D., et al., 1978 Eur J Pharmacol 47, 379-91). The Figure shows means±s.e.m. values of immobility time for control rats that received TBZ (1.5 mg/kg i.p.) and vehicle (left-hand bar on each panel) and for rats that were treated with TBZ (1.5 mg/kg i.p.) and different 5-$HT_{1A}$, receptor agonists. Befiradol (0.63 mg/kg p.o.), 1a (0.63 mg/kg p.o.) or 1b (0.63 mg/kg p.o.) or (±)8-OH-DPAT (0.63 mg/kg s.c.) significantly reduced immobility times. In contrast, buspirone (0.63 mg/kg p.o. or 2.5 mg/kg p.o.) did not reduce immobility. n.s.=not significant.

These data show that befiradol, 1a, 1b and (±)8-OH-DPAT, compounds that exhibit high agonist efficacy at 5-$HT_{1A}$ receptors, reduce depression behavior in TBZ-treated rats whereas buspirone, a compound that exhibits partial agonist efficacy at 5-$HT_{1A}$ receptors, does not.

Abbreviations: 8OH=(±)8-OH-DPAT, Bus=buspirone.

Figure 4:
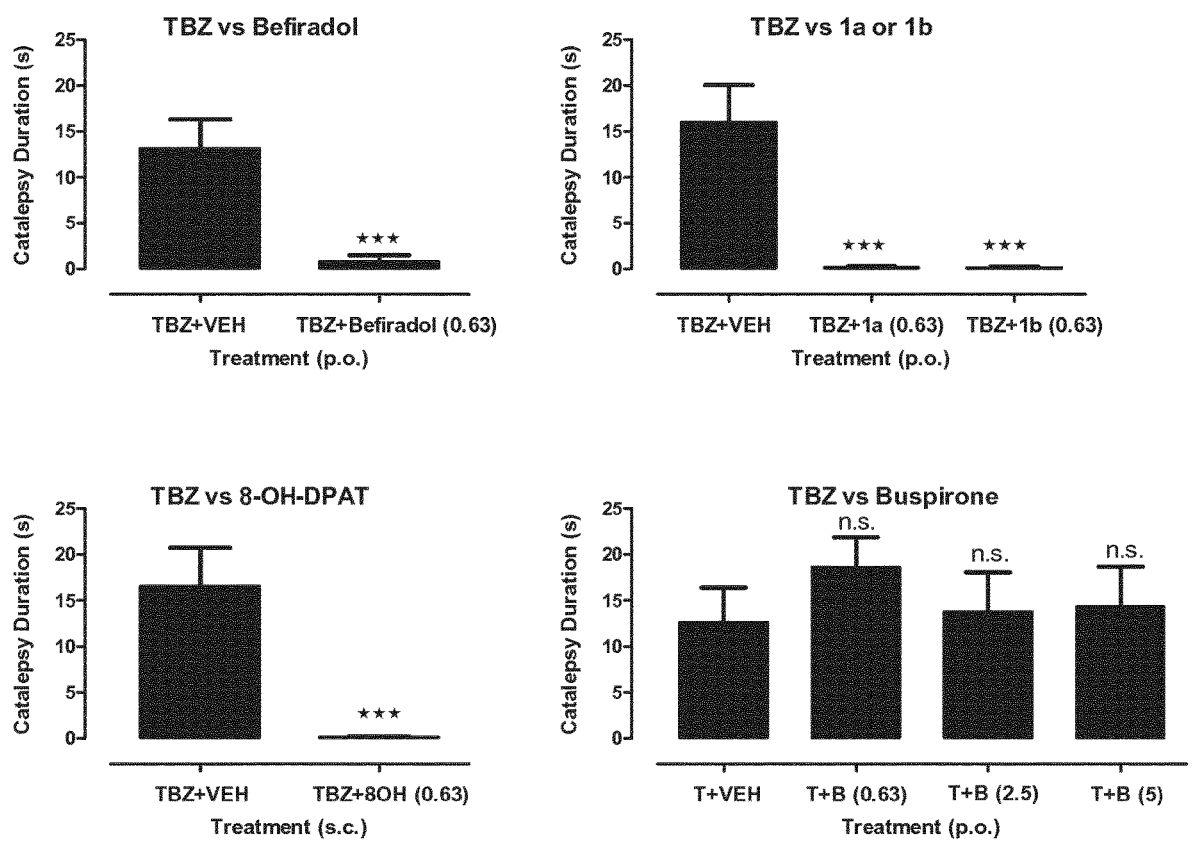

FIG. 4: Effect of serotonin 5-$HT_{1A}$ receptor agonists on TBZ-induced catalepsy behavior FIG. 4 illustrates the effects of 5-$HT_{1A}$ receptor agonists on TBZ-induced catalepsy in rat The rat Cross-Leg Position catalepsy test is an in vivo behavioral model of Parkinsonism. In this test, rats treated with TBZ (2 mg/kg i.p.) show marked catalepsy of about 15 s (left-hand bar on each panel). In contrast, rats that were treated with TBZ (2 mg/kg i.p.) and either befiradol (0.63 mg/kg p.o.), 1a (0.63 mg/kg p.o.), 1b (0.63 mg/kg p.o.) or (±)8-OH-DPAT (0.63 mg/kg s.c.) showed almost no CLP catalepsy. In contrast, buspirone does not diminish TBZ-induced catalepsy behavior. These data show that befiradol, 1a, 1b and (±)8-OH-DPAT, compounds that exhibit high agonist efficacy at 5-$HT_{1A}$, receptors, reduce catalepsy behavior in TBZ-treated rats whereas buspirone, a compound that exhibits partial agonist efficacy at 5-$HT_{1A}$, receptors, does not. n.s.=not significant.

Abbreviations: 8OH=(±)8-OH-DPAT, B=buspirone.

DETAILED DESCRIPTION OF THE INVENTION

The present invention concerns the reduction of the side-effects induced by TBZ or other inhibitors of the function of vesicular monoamine transporter (VMAT) used in the treatment of central nervous system disorders such as Huntington's disease, L-DOPA-induced dyskinesias in Parkinson's disease, Tourette's syndrome and tardive dyskinesia.

In behavioral experiments in rats, the inventors found that administration of selective serotonin 5-HT$_{1A}$, receptors agonists such as befiradol diminishes the depression behavior and the parkinsonian behavior induced by TBZ. In contrast, buspirone, a compound that acts as a partial agonist at 5-HT$_{1A}$, receptors did not diminish depression behavior or the parkinsonian behavior induced by TBZ in rat experiments.

The invention therefore consists of administering to a patient in need thereof an effective amount of a selective serotonin 5-HT$_{1A}$, receptors agonist, whereby the side-effects of depression or Parkinsonism induced by TBZ or other VMAT inhibitor are minimized.

VMAT Inhibitors

In one embodiment of the present invention, the VMAT inhibitor that can cause or aggravate side-effects including depression, suicidality and Parkinsonism is any substance capable of binding to VMAT causing it to decrease its capacity to transport neurotransmitters.

In another embodiment of the present invention, the VMAT inhibitor that can cause or aggravate side-effects including depression, suicidality and Parkinsonism is any substance capable of binding to the VMAT2 subtype of VMAT, causing it to decrease its capacity to transport neurotransmitters.

In another embodiment of the present invention, the VMAT inhibitor that can cause or aggravate side-effects including depression, suicidality and Parkinsonism is TBZ.

According to an embodiment, the side effects are depression, Parkinsonism and suicidality.

In another embodiment of the present invention, the VMAT inhibitor that can cause or aggravate side-effects including depression, suicidality and Parkinsonism is a compound selected from the following: deutetrabenazine, dihydrotetrabenazine, GZ-793A (3-[(2R,6S)-2,6-Bis[2-(4-methoxyphenyl)ethyl]-1-piperidinyl]-(2R)-1,2-propanediol), valbenazine ((2R,3R,11bR)-3-Isobutyl-9,10-dimethoxy-1,3,4,6,7,11b-hexahydro-2H-pyrido[2,1-a]isoquinolin-2-yl L-valinate) and reserpine (methyl (3β,16β,17α,18β,20α)-11,17-dimethoxy-18-[(3,4,5-trimethoxybenzoyl)oxy]yohimban-16-carboxylate).

According to an embodiment, VMAT inhibitors are selective VMAT2 inhibitors.

According to an embodiment, the VMAT inhibitor is tetrabenazine or deutetrabenazine.

5-HT$_{1A}$ Receptor Agonists

In one embodiment of the present invention, the agonist that efficaciously activates serotonin 5-HT$_{1A}$, receptors is befiradol [(3-Chloro-4-fluoro-phenyl)-[4-fluoro-4-{[(5-methyl-pyridin-2-ylmethyl)-amino]-methyl}piperidin-1-yl]methanone], or one of its pharmaceutically acceptable salts, for use as a drug that can be administered by any route which permits to obtain an effect to treat or prevent side-effects induced by VMAT inhibitors.

In another embodiment of the present invention, the agonist that efficaciously activates serotonin 5-HT$_{1A}$, receptors is either derivative 1a (3-chloro-4-fluorophenyl-[4-fluoro-4-[[(5-methylpyrimidin-2-ylmethyl)amino]methyl] piperidin-1-yl]methanone) or derivative 1b [(3-Chloro-4-fluoro-phenyl)-[4-fluoro-4-{[(5-methyl-2-methylamino-pyridin-2-ylmethyl)-amino]-methyl}piperidin-1-yl]methanone] or one of their pharmaceutically acceptable salts, for use as a drug that can be administered by any route which permits to obtain an effect to treat or prevent side-effects induced by VMAT inhibitors.

In another embodiment of the present invention, the agonist that efficaciously activates serotonin 5-HT$_{1A}$ receptors is a compound with formula (I) as defined above, or one of its pharmaceutically acceptable salts, for use as a drug that can be administered by any route which permits to obtain an effect to treat or prevent side-effects induced by VMAT inhibitors.

In another embodiment of the present invention, the agonist that efficaciously activates serotonin 5-HT$_{1A}$ receptors is a compound selected from the following: tandospirone ((1R,2R,6S,7S)-4{4-[4-(pyrimidin-2-yl)piperaZin-1-yl]butyl}-4-azatricyclo[5.2.1.02,6]decane-3,5-dione), repinotan ((R)-(—)-2-[4-[(chroman-2-ylmethyl)-amino]-butyl]-1,1-dioxo-benzo[d]isothiazolone), flesinoxan (4-fluoro-N-[2-[4-[(3S)-3(hydroxymethyl)-2,3-dihydro-1,4-benzodioxin-8-yl]piperazin-1-yl]ethyl]benzamide), flibanserin (1-(2-{4-[3(trifluoromethyl)phenyl]piperazin-1-yl}ethyl)-1,3-dihydro2H-benzimidazol-2-one), sarizotan (1-[(2R)-3,4-dihydro-2H-chromen-2-yl]-N-([5-(4fluorophenyl)pyridin-3-yl]methyl)methanamine), xaliproden (1-[2-(2-naphthyl) ethyl]-4-[3-(trifluoromethyl)phenyl]-1,2,3,6-tetrahydro-pyridine), (±)8-OH-DPAT ((±)8-hydroxy-2-(di-n-propylamino)tetralin), compound 18 described in EP16305769.8 (3-chloro-4-fluorophenyl)-4-fluoro-4-(((2-(pyridin-2-yloxy)ethyl)amino)methyl)piperidin-1-yl)methanone, or one of its pharmaceutically acceptable salts, for use as a drug that can be administered by any route which permits to obtain an effect to treat or prevent side-effects induced by VMAT inhibitors.

In another embodiment of the present invention, the agonist that efficaciously activates serotonin 5-HT$_{1A}$ receptors is a selective 5-HT$_{1A}$ agonist that exhibits a pKi value at 5-HT$_{1A}$ receptors which is 3 log units higher than the pKi value of the agonist at other 5-HT, dopaminergic, adrenergic receptors. For the purposes of example, befiradol exhibits a pKi value of about 9 at 5-HT$_{1A}$ receptors but less than 6 at other 5-HT, dopaminergic, adrenergic receptors.

In another embodiment of the present invention, the agonist that efficaciously activates serotonin 5-HT$_{1A}$ receptors is a selective 5-HT$_{1A}$ agonist that exhibits a pKi value at 5-HT$_{1A}$ receptors which is 2 log units higher than the pKi value of the agonist at other 5-HT, dopaminergic, adrenergic receptors.

In another embodiment of the present invention, the agonist that efficaciously activates serotonin 5-HT$_{1A}$ receptors is a selective 5-HT$_{1A}$ agonist that exhibits a pKi value at 5-HT$_{1A}$ receptors which is 1 log unit higher than the pKi value of the agonist at other 5-HT, dopaminergic, adrenergic receptors.

Patients

In some embodiments, the patient according to the present invention experiences one or several movement disorders. In some embodiments, the patient according to the present invention is affected or very susceptible to being or likely to become affected by a disorder entailing treatment with TBZ or other inhibitors of the function of vesicular monoamine transporter (VMAT).

According to an embodiment, the patient suffers from Huntington's disease.

According to an embodiment, the disorder of the central nervous system is Huntington's disease.

According to a further embodiment, the patient suffers from Huntington's disease and is treated with tetrabenazine or deutetrabenazine.

According to a still further embodiment, the invention concerns befiradol, derivative 1a or derivative 1b, for alleviating and/or preventing depression and suicidality in a patient suffering from Huntington's disease and treated with tetrabenazine or deutetrabenazine.

Movement Disorders

In one embodiment, the movement disorder according to the invention is selected from those associated with Huntington's disease, Parkinson's disease or Tourette's syndrome.

In another embodiment, the movement disorder according to the invention is L-DOPA-induced dyskinesia.

In another embodiment, the movement disorder according to the invention is dyskinesia induced by dopamine receptor agonists.

In another embodiment, the movement disorder according to the invention is dyskinesia induced by a dopamine enhancer.

In another embodiment, the movement disorder according to the invention is tardive dyskinesia induced by treatment with antipsychotics.

In another embodiment, the movement disorder according to the invention is associated with diseases such as, for example, Rett syndrome, Wilson's disease, Machado-Joseph disease, restless leg syndrome.

In another embodiment, the movement disorder according to the invention is selected from the group consisting of dyskinesia, chorea, ballismus, dystonia, athetosis, tics, myoclonus.

In another embodiment, the movement disorder according to the invention is associated with altered or impaired synaptic dopamine levels.

Dosing

It will be appreciated that the precise therapeutically-effective amount of $5\text{-HT}_{1A}$ receptor agonist which is necessary to obtain the desired therapeutic effect when administered to a patient will depend on age, condition, weight, etc. of the patient, the route and method of administration, the nature of the condition, disease or disorder being treated and other factors.

In some embodiments, the effective amount of befiradol according to the invention is, or is equivalent to, between 0.01 and 100 mg of befiradol base per day, preferentially between 0.1 and 10 mg of befiradol base per day, preferentially between 0.25 and 5 mg of befiradol base per day, preferentially between 0.25 and 3 mg of befiradol base per day, preferentially between 0.5 and 2 mg of befiradol base per day, preferentially between 0.5 to 1.5 mg of befiradol base per day, more preferentially 1 mg of befiradol base per day.

In some embodiments, the effective amount of tandospirone according to the invention is, or is equivalent to, between 3 and 300 mg of tandospirone base per day, preferentially between 10 and 100 mg of tandospirone base per day, more preferentially 30 mg of tandospirone base per day.

In some embodiments, the effective amount of sarizotan according to the invention is, or is equivalent to, between 0.1 and 100 mg of sarizotan base per day, preferentially between 1 and 30 mg of sarizotan base per day, preferentially between 2 and 10 mg of sarizotan base per day, more preferentially 4 mg of sarizotan base per day.

In some embodiments, the effective amount of flibanserin according to the invention is, or is equivalent to, between 10 and 1000 mg of flibanserin base per day, preferentially between 30 and 300 mg of flibanserin base per day, more preferentially 100 mg of flibanserin base per day.

It may be necessary to use doses outside these ranges as determined by the person skilled in the art.

The effective amount according to the present invention may be administered to a patient by various routes, e.g. orally, transdermally, perineurally or parenterally (e.g. by intravenous, subcutaneous, intraperitoneal, or intramuscular injection), among others, including buccal, nasal, ocular, pulmonary, sublingual, and rectal routes. It will be appreciated that the preferred route will depend on the general condition and age of the subject to be treated and the nature of the condition to be treated. In some embodiments, the effective amount according to the invention is administered orally in an appropriate formulation.

In some embodiments, the disorder according to the invention is depression or Parkinsonism induced by the administration of TBZ or another VMAT inhibitor; the patient according to the invention is affected by Huntington's disease; and the effective amount of befiradol according to the invention is, or is equivalent to, between 0.01 and 100 mg of befiradol base per day, preferentially between 0.1 and 10 mg of befiradol base per day, preferentially between 0.25 and 5 mg of befiradol base per day, preferentially between 0.25 and 3 mg of befiradol base per day, preferentially between 0.5 and 2 mg of befiradol base per day, preferentially between 0.5 to 1.5 mg of befiradol base per day, more preferentially 1 mg of befiradol base per day.

In some embodiments, the disorder according to the invention is depression or Parkinsonism induced by the administration of TBZ or another VMAT inhibitor; the patient according to the invention is affected by L-DOPA-induced dyskinesia in Parkinson's disease; and the effective amount of befiradol according to the invention is, or is equivalent to, between 0.01 and 100 mg of befiradol base per day, preferentially between 0.1 and 10 mg of befiradol base per day, preferentially between 0.25 and 5 mg of befiradol base per day, preferentially between 0.25 and 3 mg of befiradol base per day, preferentially between 0.5 and 2 mg of befiradol base per day, preferentially between 0.5 to 1.5 mg of befiradol base per day, more preferentially 1 mg of befiradol base per day.

In some embodiments, the disorder according to the invention is depression or Parkinsonism induced by the administration of TBZ or another VMAT inhibitor; the patient according to the invention is affected by Tourette's syndrome; and the effective amount of befiradol according to the invention is, or is equivalent to, between 0.01 and 100 mg of befiradol base per day, preferentially between 0.1 and 10 mg of befiradol base per day, preferentially between 0.25 and 5 mg of befiradol base per day, preferentially between 0.25 and 3 mg of befiradol base per day, preferentially between 0.5 and 2 mg of befiradol base per day, preferentially between 0.5 to 1.5 mg of befiradol base per day, more preferentially 1 mg of befiradol base per day.

In some embodiments, the disorder according to the invention is depression or Parkinsonism induced by the administration of TBZ or another VMAT inhibitor; the patient according to the invention is affected by tardive dyskinesia; and the effective amount of befiradol according to the invention is, or is equivalent to, between 0.01 and 100 mg of befiradol base per day, preferentially between 0.1 and 10 mg of befiradol base per day, preferentially between 0.25 and 5 mg of befiradol base per day, preferentially between 0.25 and 3 mg of befiradol base per day, preferentially between 0.5 and 2 mg of befiradol base per day, preferentially between 0.5 to 1.5 mg of befiradol base per day, more preferentially 1 mg of befiradol base per day.

The administration according to the present invention can be once a day or several times throughout the day, preferentially once a day or twice a day in equal doses.

In some embodiments, the disorder according to the invention is depression or Parkinsonism induced by the administration of TBZ or another VMAT inhibitor; the patient according to the invention is affected by Huntington's disease; and the effective amount of tandospirone according to the invention is, or is equivalent to, between 3 and 300 mg of tandospirone base per day, preferentially between 10 and 100 mg of tandospirone base per day, more preferentially 30 mg of tandospirone base per day.

In some embodiments, the disorder according to the invention is depression or Parkinsonism induced by the administration of TBZ or another VMAT inhibitor; the patient according to the invention is affected by L-DOPA-induced dyskinesia in Parkinson's disease; and the effective amount of tandospirone according to the invention is, or is equivalent to, between 3 and 300 mg of tandospirone base per day, preferentially between 10 and 100 mg of tandospirone base per day, more preferentially 30 mg of tandospirone base per day.

In some embodiments, the disorder according to the invention is depression or Parkinsonism induced by the administration of TBZ or another VMAT inhibitor; the patient according to the invention is affected by Tourette's syndrome; and the effective amount of tandospirone according to the invention is, or is equivalent to, between 3 and 300 mg of tandospirone base per day, preferentially between 10 and 100 mg of tandospirone base per day, more preferentially 30 mg of tandospirone base per day.

In some embodiments, the disorder according to the invention is depression or Parkinsonism induced by the administration of TBZ or another VMAT inhibitor; the patient according to the invention is affected by tardive dyskinesia; and the effective amount of tandospirone according to the invention is, or is equivalent to, between 3 and 300 mg of tandospirone base per day, preferentially between 10 and 100 mg of tandospirone base per day, more preferentially 30 mg of tandospirone base per day.

The administration according to the present invention can be once a day or several times throughout the day, preferentially once a day or twice a day in equal doses.

In some embodiments, the disorder according to the invention is depression or Parkinsonism induced by the administration of TBZ or another VMAT inhibitor; the patient according to the invention is affected by Huntington's disease; and the effective amount of sarizotan according to the invention is, or is equivalent to, between 0.1 and 100 mg of sarizotan base per day, preferentially between 1 and 30 mg of sarizotan base per day, preferentially between 2 and 10 mg of sarizotan base per day, more preferentially 4 mg of sarizotan base per day.

In some embodiments, the disorder according to the invention is depression or Parkinsonism induced by the administration of TBZ or another VMAT inhibitor; the patient according to the invention is affected by L-DOPA-induced dyskinesia in Parkinson's disease; and the effective amount of sarizotan according to the invention is, or is equivalent to, between 0.1 and 100 mg of sarizotan base per day, preferentially between 1 and 30 mg of sarizotan base per day, preferentially between 2 and 10 mg of sarizotan base per day, more preferentially 4 mg of sarizotan base per day.

In some embodiments, the disorder according to the invention is depression or Parkinsonism induced by the administration of TBZ or another VMAT inhibitor; the patient according to the invention is affected by Tourette's syndrome; and the effective amount of sarizotan according to the invention is, or is equivalent to, between 0.1 and 100 mg of sarizotan base per day, preferentially between 1 and 30 mg of sarizotan base per day, preferentially between 2 and 10 mg of sarizotan base per day, more preferentially 4 mg of sarizotan base per day.

In some embodiments, the disorder according to the invention is depression or Parkinsonism induced by the administration of TBZ or another VMAT inhibitor; the patient according to the invention is affected by tardive dyskinesia; and the effective amount of sarizotan according to the invention is, or is equivalent to, between 0.1 and 100 mg of sarizotan base per day, preferentially between 1 and 30 mg of sarizotan base per day, preferentially between 2 and 10 mg of sarizotan base per day, more preferentially 4 mg of sarizotan base per day.

The administration according to the present invention can be once a day or several times throughout the day, preferentially once a day or twice a day in equal doses.

In some embodiments, the disorder according to the invention is depression or Parkinsonism induced by the administration of TBZ or another VMAT inhibitor; the patient according to the invention is affected by Huntington's disease; and the effective amount of flibanserin according to the invention is, or is equivalent to, between 10 and 1000 mg of flibanserin base per day, preferentially between 30 and 300 mg of flibanserin base per day, more preferentially 100 mg of flibanserin base per day.

In some embodiments, the disorder according to the invention is depression or Parkinsonism induced by the administration of TBZ or another VMAT inhibitor; the patient according to the invention is affected by L-DOPA-induced dyskinesia in Parkinson's disease; and the effective amount of flibanserin according to the invention is, or is equivalent to, between 10 and 1000 mg of flibanserin base per day, preferentially between 30 and 300 mg of flibanserin base per day, more preferentially 100 mg of flibanserin base per day.

In some embodiments, the disorder according to the invention is depression or Parkinsonism induced by the administration of TBZ or another VMAT inhibitor; the patient according to the invention is affected by Tourette's syndrome; and the effective amount of flibanserin according to the invention is, or is equivalent to, between 10 and 1000 mg of flibanserin base per day, preferentially between 30 and 300 mg of flibanserin base per day, more preferentially 100 mg of flibanserin base per day.

In some embodiments, the disorder according to the invention is depression or Parkinsonism induced by the administration of TBZ or another VMAT inhibitor; the patient according to the invention is affected by tardive dyskinesia; and the effective amount of flibanserin according to the invention is, or is equivalent to, between 10 and 1000 mg of flibanserin base per day, preferentially between 30 and 300 mg of flibanserin base per day, more preferentially 100 mg of flibanserin base per day.

The administration according to the present invention can be once a day or several times throughout the day, preferentially once a day or twice a day in equal doses.

Compositions

The composition according to the invention can comprise any effective amount of active pharmaceutical ingredient and/or one or more pharmaceutically acceptable derivatives thereof. Methods for preparing such dosage forms are known or will be apparent to those skilled in the art.

In some embodiments, the composition according to the invention comprises between 0.01 and 100 mg of befiradol and/or one or more pharmaceutically acceptable derivatives, expressed as equivalent amount of befiradol base, preferentially between 0.1 and 10 mg, preferentially between 0.25 and 3 mg, preferentially between 0.5 and 2 mg, preferentially between 0.5 to 1.5 mg, more preferentially 0.5 mg, more preferentially 1 mg.

In some embodiments, the composition according to the invention comprises between 3 and 300 mg of tandospirone and/or one or more pharmaceutically acceptable derivatives, expressed as equivalent amount of tandospirone base, preferentially between 10 and 100 mg, more preferentially 30 mg.

In some embodiments, the composition according to the invention comprises between 0.1 and 100 mg of sarizotan and/or one or more pharmaceutically acceptable derivatives, expressed as equivalent amount of sarizotan base, preferentially between 1 and 30 mg, preferentially between 2 and 10 mg, more preferentially 4 mg.

In some embodiments, the composition according to the invention comprises between 10 and 1000 mg of flibanserin and/or one or more pharmaceutically acceptable derivatives, expressed as equivalent amount of flibanserin base, preferentially between 30 and 300 mg, more preferentially 100 mg.

The composition according to the present invention may be administered to a patient by various routes, e.g. orally, transdermally, perineurally or parenterally (e.g. by intravenous, subcutaneous, intraperitoneal, or intramuscular injection), among others, including buccal, nasal, ocular, pulmonary, sublingual, and rectal routes. It will be appreciated that the preferred route will depend on the general condition and age of the subject to be treated and the nature of the condition to be treated. In some embodiments, the composition according to the invention is administered orally in an appropriate formulation.

The composition according to the present invention may take the form of solid, semi-solid, lyophilized powder, or liquid dosage forms, such as, for example, tablets, hard and soft capsules, pills, lozenges, powders, granules, solutions, suspensions, emulsions, syrups, elixirs, suppositories, creams, ointments, lotions, gels, aerosols, patches, implants or the like, preferentially in one or more unit dosage forms suitable for simple administration of precise dosages. In some embodiments, the composition according to the invention takes the form of loaded capsules, preferentially hydroxypropyl cellulose or gelatin capsules.

In some embodiments, the method according to the invention comprises administering to the patient at least one sustained release composition of active pharmaceutical ingredient or a pharmaceutically acceptable derivative thereof.

The composition according to the invention can comprise, depending on the intended mode of administration and the specific formulation, any suitable weight percentage of active pharmaceutical ingredient and/or one or more pharmaceutically acceptable derivatives thereof, with respect to the total weight of the composition.

In some embodiments, the dosage form according to the invention comprises about 0.001% to about 95% by weight of active pharmaceutical ingredient and/or one or more pharmaceutically acceptable derivatives thereof, with respect to the total weight of the composition, preferentially about 0.05% to about 50%, preferentially about 0.5% to about 25%, preferentially about 1% to about 10%, preferentially about 1% to about 5%, preferentially about 1% to about 2.5%, with the remainder consisting essentially of pharmaceutically acceptable excipients. Optionally, the composition according to the present invention may further include other medicinal agents.

The foregoing invention has been described by way of illustration and example for purposes of clarity of understanding, but it will be readily apparent to those of ordinary skill in the art in light of the teachings of this invention that certain changes and modifications may be made thereto without departing from the spirit or scope of the appended claims.

EXAMPLES

Example 1

Determination of in Vitro Agonist Efficacy at Serotonin 5-HT$_{1A}$ Receptors G-protein Activation Assay Agonist efficacy for stimulation of G-protein activation at serotonin 5-HT$_{1A}$ receptors can be determined by [$^{35}$S]GTPγS binding assays as follows. Experiments employed brains of male Sprague-Dawley rats which were stored at −70° C. before use in binding assays. Experiments were carried out in triplicate and repeated at least three times. Frozen brains were thawed in ice-cold buffer A (50 mM Hepes containing 150 mM NaCl, 0.2 mM EDTA, 1 mM GTP, 10 μM pargyline; pH 7.4, 23° C.). Hippocampi were dissected and homogenized in 20 volumes of buffer A before incubation at 37° C. for 10 min to dissociate endogenous neurotransmitters from receptors. The homogenate was centrifuged at 20 000 g for 15 min, at 4° C. The pellet was re-suspended in buffer A and recentrifuged as before. The pellet was then re-suspended in buffer B (50 mM Hepes containing 150 mM NaCl, 0.2 mM EDTA, 5 mM MgCl$_2$, 100 μM GDP, 10 μM pargyline), centrifuged as before and re-suspended in buffer B. Membranes were incubated in buffer B with test compounds and 0.1 nM [$^{35}$S]GTPγS for 60 min at 37° C. The incubation was terminated by rapid filtration through Whatman GF-B fiber filters using a Brandel harvester. Radioactivity retained on the filters was measured by liquid scintillation counting. Data were analyzed using a nonlinear curve-fitting program (Prism, Graphpad Software, San Diego, Calif., USA), and are expressed as mean value±S.E.M.

Agonist efficacy is expressed as Emax values and corresponds to the amount of [$^{35}$S]GTPγS binding observed at a maximally-effective concentration of the agonists (10 μM). Emax values are expressed as % of the stimulation induced by the endogenous agonist, serotonin (5-HT, 10 μM) which was tested as a standard in each experiment.

It should be noted that 5-HT can activate different 5-HT receptors. Herein, only the proportion of 5-HT's effect which is 5-HT$_{1A}$ receptor-dependent was considered in the calculations. This was determined in [$^{35}$S]GTPγS binding experiments by co-incubating 5-HT with the selective 5-HT$_{1A}$ receptor antagonist, WAY100635 (1 μM). The latter reduced 5-HT-induced [$^{35}$S]GTPγS binding to 15%. Thus, 85% of 5-HT-induced [$^{35}$S]GTPγS binding was mediated by 5-HT$_{1A}$ receptors.

Results

Figure 1:
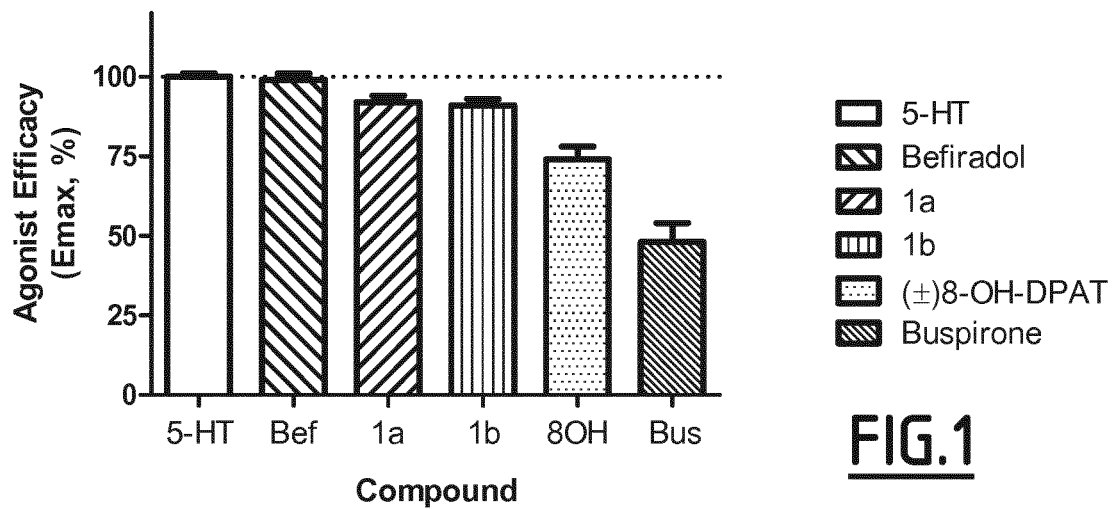
FIG. 1: Effects of 5-$HT_{1A}$ receptor agonists on [$^{35}$S]GTPγS binding

The endogenous agonist, 5-HT, stimulated [$^{35}$S]GTPγS binding with an efficacy that was defined as 100%. Befiradol, 1a and 1b exhibited high agonist efficacy (see FIG. 1). That is, they stimulated [$^{35}$S]GTPγS binding with Emax values that were greater than 90% relative to 5-HT. In contrast, buspirone behaved as a partial agonist with efficacy of only about 50%. (±)8-OH-DPAT exhibited efficacy that was intermediate between that of buspirone and the other compounds.

Example 2

Study of Depression Behavior in the Forced Swim Test in Rats Treated with TBZ

Animals

The experiments were performed on male Wistar rats (170-200 g) obtained from an accredited animal facility at the Jagiellonian University Medical College, Poland. The animals were housed in group of four in controlled environment (ambient temperature 21±20 C; relative humidity 55%±10%; 12-h light/dark cycles (lights on at 8:00). Standard laboratory food (LSM-B) and filtered water were freely available. Animals were assigned randomly to treatment groups. All the experiments were performed by two observers unaware of the treatment applied between 9:00 and 14:00 on separate groups of animals. All animals were used only once. All the experimental procedures complied with the European Communities Council Directive of 24 Nov. 1986 (86/609/EEC) and were in accordance with the 1996 NIH Guide for the Care and Use of Laboratory Animals.

Drugs

Tetrabenazine (TBZ) was dissolved in a vehicle solution of 0,9% saline and dimethylsulfoxide (DMSO) (20%). 10 µl hydrochloric acid (HCl) was then added to achieve full solubilization of the drug. TBZ (1.5 mg/kg) was administered intraperitoneally (i.p.).

Forced Swim Test (FST)

The experiment was carried out according to a well-characterized method (Porsolt et al., 1978). On the first day of an experiment, the animals (at least n=6 per group) were gently individually placed in Plexiglas cylinders (40 cm high, 18 cm in diameter) containing water (17 cm deep) maintained at 23-25° C. for 15 min. On removal from water, the rats were placed for 30 min in a Plexiglas box under a 60 W incandescent filament bulb to dry. On the following day (24 h later), TBZ (1.5 mg/kg) was administered to rats by intraperitoneal (i.p.) route 90 min before testing. For testing, rats were re-placed in the cylinder and the total duration of their immobility was recorded during a 5-min test period. The swimming behavior entailed active swimming motions, e.g., moving horizontally around in the cylinder, and immobility was assigned when no additional activity was observed other than that necessary to keep the rat's head above the water. Fresh water was used for each animal.

Results

Figure 2:
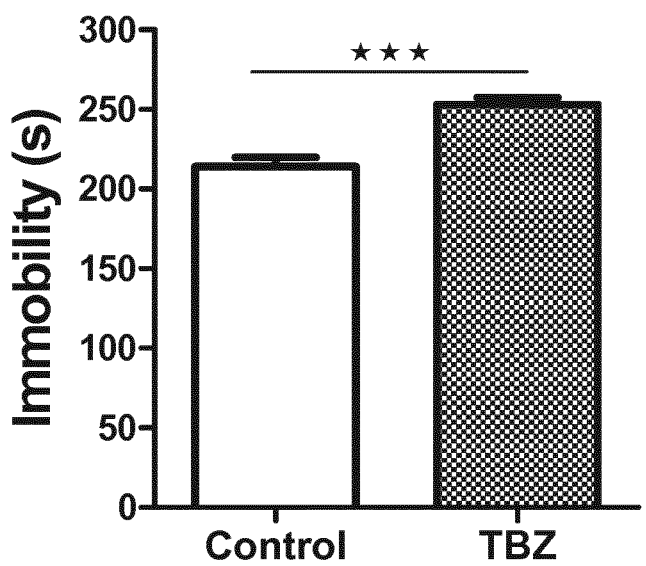
FIG. 2: Increased depression behavior induced by TBZ in the Forced Swim Test

Rats in the control group (treated only with vehicle) exhibited average immobility times of 214 s. In contrast, rats in the test group (i.e. treated with TBZ) exhibited an average duration of immobility of about 250 s (FIG. 2). Statistical analysis (unpaired t-test) indicated a highly significant treatment effect (unpaired t-test; t(87)=5.41, p<0.0001). These results show that treatment with TBZ increases depression behavior in rats.

Example 3

Study of the Effects of Serotonin 5-HT$_{1A}$ Receptor Agonists on Depression Behavior in TBZ-Treated Rats in the Forced Swim Test Animals The experiments were performed on male Wistar rats (170-200 g) obtained from an accredited animal facility at the Jagiellonian University Medical College, Poland. The animals were housed in group of four in controlled environment (ambient temperature 21±20 C; relative humidity 55%±10%; 12-h light/dark cycles (lights on at 8:00). Standard laboratory food (LSM-B) and filtered water were freely available. Animals were assigned randomly to treatment groups. All the experiments were performed by two observers unaware of the treatment applied between 9:00 and 14:00 on separate groups of animals. All animals were used only once. All the experimental procedures complied with the European Communities Council Directive of 24 Nov. 1986 (86/609/EEC) and were in accordance with the 1996 NIH Guide for the Care and Use of Laboratory Animals.

Drugs

Tetrabenazine (TBZ) was dissolved in a vehicle solution of 0.9% saline and dimethylsulfoxide (DMSO) (20%). 10-µl hydrochloric acid (HCl) was then added to achieve full solubilization of the drug. TBZ (1.5 mg/kg) was administered intraperitoneally (i.p.).

Befiradol, 1a, 1b and buspirone were dissolved in distilled water and were given orally (p.o.). (±)8-OH-DPAT, which is poorly bioavailable by oral route (Mason, J. P., 1995 Xenobiotica. 25, 1371-80), was dissolved in distilled water and administered subcutaneously (s.c.). All compounds were given in a volume of 2 ml/kg. All compounds were tested at the dose of 0.63 mg/kg. Buspirone was also tested at the dose of 2.5 mg/kg.

Forced Swim Test (FST)

The experiment was carried out according to a well-characterized method (Porsolt, R. D., et al., 1978 Eur J Pharmacol 47, 379-91). On the first day of an experiment, the animals (at least n=6 per group) were gently individually placed in Plexiglas cylinders (40 cm high, 18 cm in diameter) containing water (17 cm deep) maintained at 23-25° C. for 15 min. On removal from water, the rats were placed for 30 min in a Plexiglas box under a 60 W incandescent filament bulb to dry. On the following day (24 h later), TBZ (1.5 mg/kg) was administered to rats by intraperitoneal (i.p.) route 90 min before testing. Serotonin 5-HT$_{1A}$ receptor agonists were then administered to rats by oral administration (p.o.) 60 minutes before the rats were re-placed in the cylinder and the total duration of their immobility was recorded during the 5-min test period. The swimming behavior entailed active swimming motions, e.g., moving horizontally around in the cylinder, and immobility was assigned when no additional activity was observed other than that necessary to keep the rat's head above the water.

Results

Figure 3:
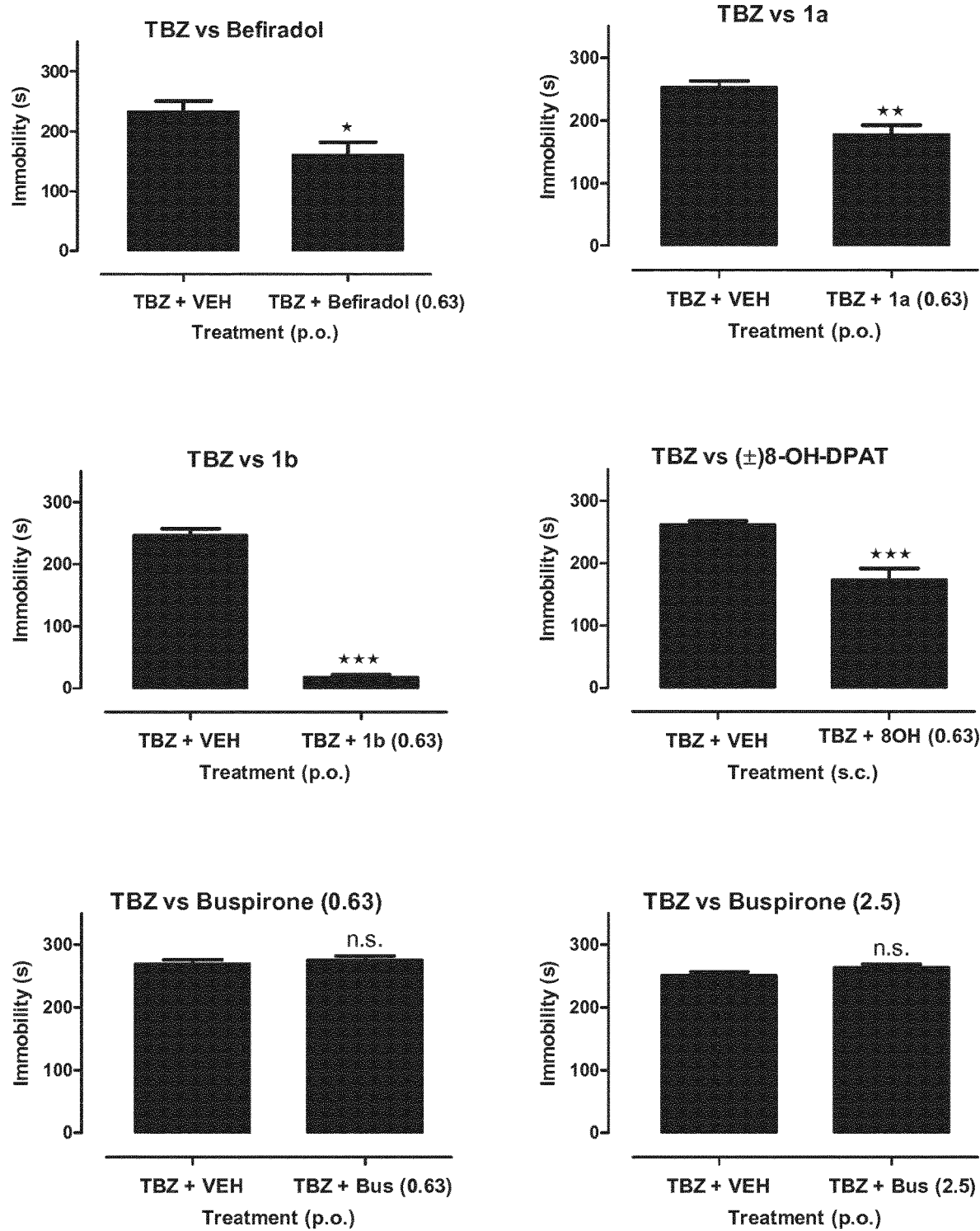
FIG. 3: Effects of serotonin 5-$HT_{1A}$ receptor agonists on depression behavior in TBZ-treated rats in the Forced Swim Test

Rats in the control groups (i.e. treated with TBZ and vehicle) exhibited average immobility times of approximately 250 s (FIG. 3). In contrast, rats treated with TBZ and either befiradol, 1a, 1b or (±)8-OH-DPAT exhibited significantly decreased durations of immobility. Rats were also treated with TBZ and different doses buspirone (0.63 or 2.5 mg/kg) in a range known to be active in vivo (Vaidya, A. H., et al., 2005 Methods Find Exp Clin Pharmacol. 27, 245-55). Buspirone did not reduce immobility duration significantly from that of the respective control groups (see statistical information below).

These results indicate that some 5-HT$_{1A}$ receptor agonists can attenuate TBZ-induced depression behavior.

| Compound | Statistical Results: unpaired t-test |
|---|---|
| Befiradol (0.63 mg/kg) | t(14) = 2.68, p < 0.05 |
| 1a (0.63 mg/kg) | t(14) = 4.13, p < 0.01 |
| 1b (0.63 mg/kg) | t(13) = 18.1, p < 0.001 |
| (±)8-OH-DPAT (0.63 mg/kg) | t(14) = 4.62, p < 0.001 |
| Buspirone (0.63 mg/kg) | t(13) = 0.657, p > 0.05, not significant |
| Buspirone (2.5 mg/kg) | t(13) = 1.52, p > 0.05, not significant |

Example 4

Effect of Serotonin 5-HT$_{1A}$ Receptor Agonists on TBZ-Induced Catalepsy Behavior Animals and Drugs Animals were obtained, housed and handled according to the same protocols described for Example 3. Similarly, drugs were prepared and administered according to the same protocols described for Example 3. All compounds were tested at the dose of 0.63 mg/kg. Buspirone was also tested at the doses of 2.5 and 5 mg/kg.

Cross-Legged Position Catalepsy Test

Catalepsy induction in rats is a recognized model of Parkinsonism (Duty, S., 2011 Br J Pharmacol. 164, 1357-91). Here, catalepsy was measured using the cross-legged position test (CLP test) according to the method described by (Prinssen, E. P., et al., 1998 Eur J Pharmacol. 356, 189-92). Serotonin 5-HT$_{1A}$ receptor agonists were administered to rats (at least 6 per group) by oral administration (p.o.) 55 minutes before the CLP test, TBZ (2 mg/kg) was administered to rats by intraperitoneal (i.p.) route 30 min before testing. In the CLP test, the hind-limbs were placed over the ipsilateral forelimbs and the time during which an animal remained in this position was determined up to maximum of 30 seconds. The test was repeated three times (inter-trial time: 3 minutes) and the mean of the three trials was used for analysis. Animals were put back in their home cage after each set of tests.

Results

Rats in the control groups (i.e. treated with TBZ and vehicle) exhibited average CLP catalepsy times of approximately 15 s (FIG. 4). In contrast, rats treated with TBZ and either befiradol or (±)8-OH-DPAT exhibited significantly decreased durations of immobility (412)=4.38, p<0.001 and t(13)=4.91, p<0.001, respectively; 2-tailed t-test). Rats treated with TBZ and either 1a or 1b also showed significantly decreased durations of catalepsy. Indeed, one-way ANOVA indicated a highly significant effect of treatment (F(2,21)=15.67, p<0.0001) and Dunnet's post-hoc test indicated that both agonists significantly reduced catalepsy from control values (p<0.05). Rats were also treated with TBZ and different doses buspirone (0.63, 2.5 or 5 mg/kg) in a range known to be active in vivo (Vaidya, A. H., et al., 2005 Methods Find Exp Clin Pharmacol. 27, 245-55). None of the doses of buspirone showed durations of catalepsy that differed significantly from those of the control group (one-way ANOVA F(3,28)=0.4439, p>0.05).

These results indicate that some 5-HT$_{1A}$ receptor agonists can attenuate TBZ-induced catalepsy, an animal model associated with Parkinsonism.

The invention claimed is:

1. A method for alleviating one or more Vesicular Monoamine Transporter (VMAT) inhibitor-induced side-effect in a central nervous system disorder patient treated with one or more VMAT inhibitor comprising administering a selective 5-HT$_{1A}$ receptor agonist, wherein the VMAT inhibitor is tetrabenazine (TBZ) or deutetrabenazine and the selective 5-HT$_{1A}$ receptor agonist is selected from the group consisting of befiradol, derivative 1a (3-chloro-4-fluorophenyl-[4-fluoro-4-[[(5-methylpyrimidin-2-ylmethyl)amino]methyl]piperidin-1-yl]methanone), and derivative 1b [(3-Chloro-4-fluoro-phenyl)-[4-fluoro-4-{[(5-methyl-2-methylamino-pyridin-2-ylmethyl)-amino]-methyl}piperidin-1-yl]methanone]:

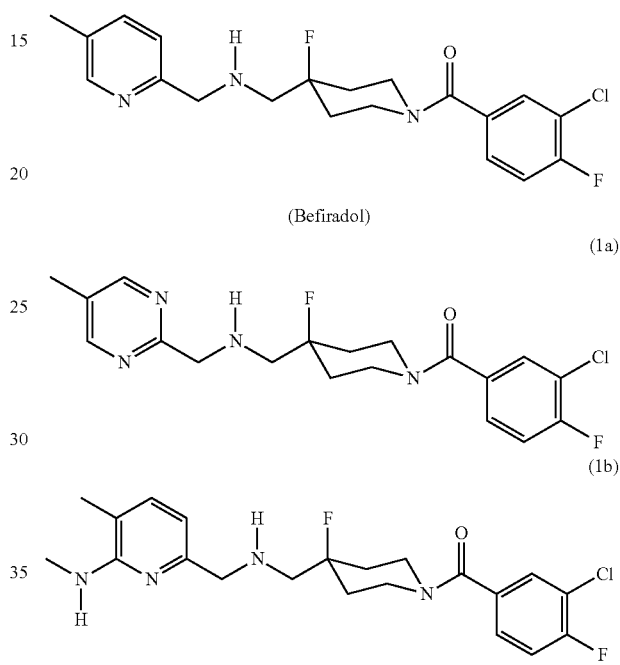

and their pharmaceutically acceptable salts, wherein the VMAT inhibitor-induced side-effect is selected from the group consisting of depression, suicidality, extrapyramidal symptoms and Parkinsonism.

2. The method according to claim 1, wherein said selective 5-HT$_{1A}$ receptor agonist selectively activates serotonin 5-HT$_{1A}$ receptors in an in vitro assay in a greater extent than the activation elicited by the partial agonist, buspirone.

3. The method according to claim 1, wherein the selective 5-HT$_{1A}$ receptor agonist is befiradol or a pharmaceutically acceptable salt thereof.

4. The method according to claim 3, wherein befiradol or a pharmaceutically acceptable salt thereof is administered orally.

5. The method according to claim 3, wherein befiradol or a pharmaceutically acceptable salt thereof is formulated as a sustained release pharmaceutical composition.

6. The method according to claim 1, wherein the central nervous system disorder is selected from the group consisting of Huntington's disease, L-DOPA-induced dyskinesias in Parkinson's disease, Tourette's syndrome and tardive dyskinesia.

* * * * *